(12) United States Patent
Saha

(10) Patent No.: US 8,419,640 B1
(45) Date of Patent: Apr. 16, 2013

(54) REMOVAL OF BONE CEMENT AND IMPLANTS BY ULTRASONIC VIBRATION METHODS

(76) Inventor: Subrata Saha, Brooklyn, NY (US)

(*) Notice: Subject to any disclaimer, the term of this patent is extended or adjusted under 35 U.S.C. 154(b) by 706 days.

(21) Appl. No.: 12/583,403

(22) Filed: Aug. 20, 2009

Related U.S. Application Data

(60) Provisional application No. 61/189,669, filed on Aug. 21, 2008.

(51) Int. Cl.
*A61B 8/00* (2006.01)

(52) U.S. Cl.
USPC .............................. 600/437; 600/439; 600/443

(58) Field of Classification Search .................. 600/437, 600/439, 443
See application file for complete search history.

(56) References Cited

U.S. PATENT DOCUMENTS

| | | | |
|---|---|---|---|
| 6,932,308 B2 * | 8/2005 | Talish et al. | 248/226.11 |
| 7,544,166 B2 * | 6/2009 | Yuan et al. | 600/466 |
| 2002/0099288 A1 * | 7/2002 | Chang et al. | 600/439 |
| 2007/0238998 A1 * | 10/2007 | Nycz et al. | 600/437 |
| 2008/0228077 A1 * | 9/2008 | Wilk et al. | 600/447 |

\* cited by examiner

*Primary Examiner* — Unsu Jung
*Assistant Examiner* — Joel Lamprecht
(74) *Attorney, Agent, or Firm* — James Creighton Wray

(57) ABSTRACT

A transducer supplies high frequency or low frequency vibrations to an implant for facilitating its removal or insertion in body tissue. The vibrations are conducted through a horn with a tip conformed to the implant. Loosening rods, screws and plates from healing bone uses a transducer or horn adjacent or around a limb.

27 Claims, 3 Drawing Sheets

REMOVAL OF BONE CEMENT AND IMPLANTS BY ULTRASONIC VIBRATION METHODS

This application claims the benefit of U.S. Provisional Application No. 61/189,669, filed Aug. 21, 2008, which is hereby incorporated by reference in its entirety.

BACKGROUND OF THE INVENTION

Total joint arthroplasty, particularly total hip and total knees are being performed at an increasing rate in United States and in other developed countries. The estimated numbers are between 250,000 and 350,000 per year for each of the hip and knee joints. It is also estimated that about 10% of these joints fail at the end of ten years, and the failure rates increase with longer years of use. Due to the rapid increase in geriatric population, the number of patients requiring revision of a failed knee or hip arthroplasty is increasing.

In most total knee replacements, the majority of total hip joint replacements, and most other joint replacements, the implant is fixed to the bone with the help of a self curing acrylic cement (polymethylmethacrylate) called bone cement. In the revision surgery, the removal of the existing implant, reconstruction of the bone-stock and achievement of a stable fixation with a new component is often a difficult procedure. This is because bone cement is sometimes firmly bonded to the implant and surrounding bone, making it a technically demanding process to remove the implant without damaging the surrounding bone. For un-cemented hip and other joints, the implant is again firmly fixed to the bone, often due to in growth of bony tissue into the porous surface of the metal implant. The goal of such revision surgery is to remove the implant with minimum damage to the bone tissue. This is because the new implant needs bony support to be successful. Sometimes the difficulty in removing an implant causes the bone to fracture, and occasionally implant removal requires the surgeon to cut the bone itself to remove the implant. Thus, there is a definite need for new instrumentation to facilitate the removal of a cemented or un-cemented implant that will cause minimal damage to the bone tissue.

Needs exist for improved methods and apparatus for removing and inserting bone implants and rods, screws, plates and tooth and soft tissue implants.

SUMMARY OF THE INVENTION

It is the object of this invention to overcome the above identified problems in the related art and to provide apparatus and methods for easier removal of cemented and un-cemented total joints and other implants. It is a further object of this invention to provide methods and apparatus for removal of implants that have been used for fracture fixation and need to be removed after the bone has healed. Examples of such implants are intramedullary rods and fracture fixation plates.

In a general embodiment, the present invention provides of a generator that acts as a power supply to a transducer that produces a vibration from low a few hundred Hz. to high many thousand Hz. frequency. The vibrations are transmitted to a horn whose size and shape depends on the particular application. The tip of the horn fits the area of the implant where it will be attached. For example, the tip of the horn may have a cup shape to fit a ball joint of a total hip implant. The horn tip can also be the shape of a full or partial ring to attach the vibrator to the neck area of a femoral component of an artificial hip joint. This ring shaped tip can be flexible, hinged or rigid and of a variety of sizes. Similarly, the tip can be concave or convex or combination of both shapes to apply the vibration to the cup of a hip joint, to an artificial knee joint or to shoulder joint. The tip of the horn can also be made of material that will mold to the area of application.

In an alternative embodiment, the limb or the body part containing the implant will be subjected to an ultrasonic energy above 20,000 Hz or vibratory energy below 20,000 Hz, depending on the particular application for producing a heating effect at the interface of the implant and the surrounding tissue. The heating effect is caused as part of the ultrasonic pulse that is reflected and dissipated at the interface, due to the mismatch of impedance. The increased temperature produces a thermal damage to the tissue at the interface, activating tissue destroying cells, such as osteoclasts for bone tissue. After several weeks, the tissue will resorb, and the implant will require less force to be removed. The tissue destruction can also be caused by the mechanical damage, due to microfractures produced by the vibratory or ultrasonic stimulation.

These and further and other objects and features of the invention are apparent in the disclosure, which include the above and ongoing written specification, with the claims and the drawings.

DETAILED DESCRIPTION OF THE DRAWINGS

Figure 1:
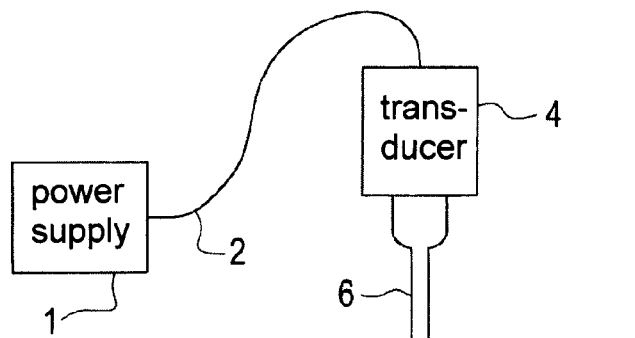
FIG. 1 is a general schematic representation of the invention ready to contact an implant head for use before removal of an artificial hip implant.

FIG. 1 shows a power supply 1 connected by an electric wire or wires 2 to a transducer 4. The transducer is connected to a horn 6 intended to be applied to the artificial head of a hip implant 10. Also shown is the neck 11 of the artificial hip joint 10, the stem 13 of the artificial hip joint, the bone cement 15 holding the artificial hip joint in place, and the surface bone 18.

The power supply 1 provides power to the transducer 4 that produces ultrasonic or subsonic vibration through the horn 6 that is applied to the head 9 of the artificial joint 10. That in turn transmits the vibration down through the neck 11 and the stem 13, causing the implant 10 to be released from the hold of the bone cement 15 so that the artificial hip joint can be removed from the bone 18. The transducer 4 can be made of single or multiple piezoelectric ceramic parts, for example, PZT parts that are often used for ultrasonic transducers. Transducer 4 can also be made of electromagnetic coils that can produce a cyclic vibratory motion.

Figure 2:
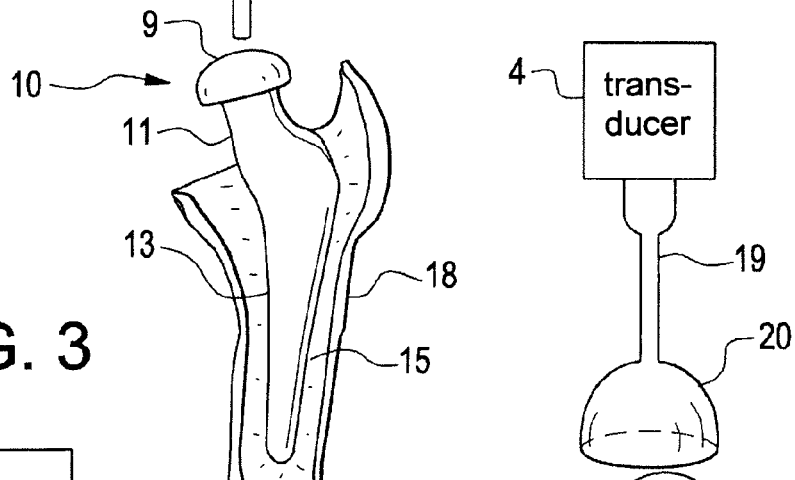
FIG. 2 is a depiction of an embodiment with a cup shaped tip of the horn.

FIG. 2 shows a cup shaped tip 20 of a horn 19 that fits over the artificial head 9 of the hip joint 10. The power supply 1 provides power to the transducer 4 that produces ultrasonic vibration through the horn 19 that is applied to the head 9 of the artificial joint. That in turn transmits the vibration from horn 19 down through the neck 11 and the stem 13, causing the hip joint artificial implant to be released from the hold of the bone cement 15 so that the implant 10 can be removed from the bone 18.

Figure 3:
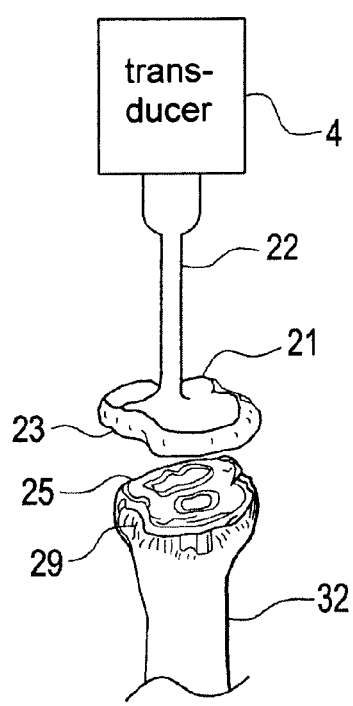
FIG. 3 is a depiction of an embodiment showing a horn tip with convex and concave surfaces to make more adequate contact with the surfaces of an implant such as that implanted in a knee joint.
Figure 3:
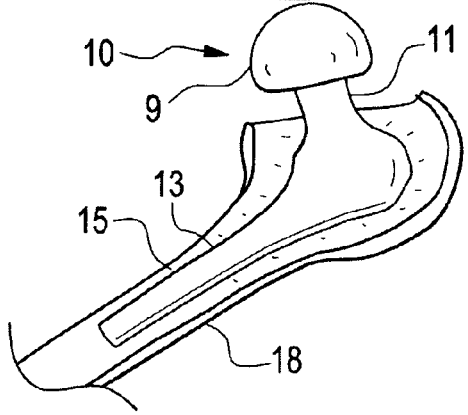

FIG. 3 shows a tip of the horn shaped with convex and concave surfaces 23 in order to make smooth and more efficient contact with the artificial knee implant 25 that is held in place with bone cement 29 within the bone 32. The power supply 1 provides power to the transducer 4 that produces ultrasonic vibration through the horn 22 tip 21 and surfaces 23. The ultrasonic vibrations are applied to the surface of the artificial joint 25. That in turn transmits the vibrations down through the body of the artificial joint, causing the implant to be released from the hold of the bone cement 29 so that it can be removed from the bone 32.

Figure 4A:
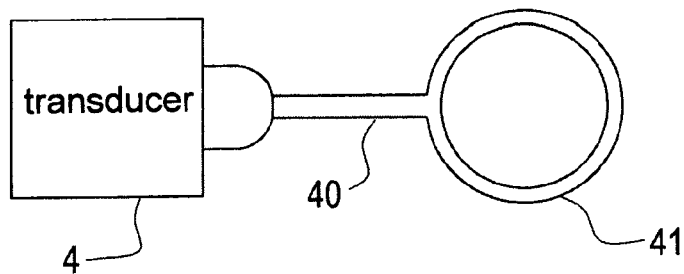
FIGS. 4A, B and C show a ring shaped horn tips.
Figure 4B:
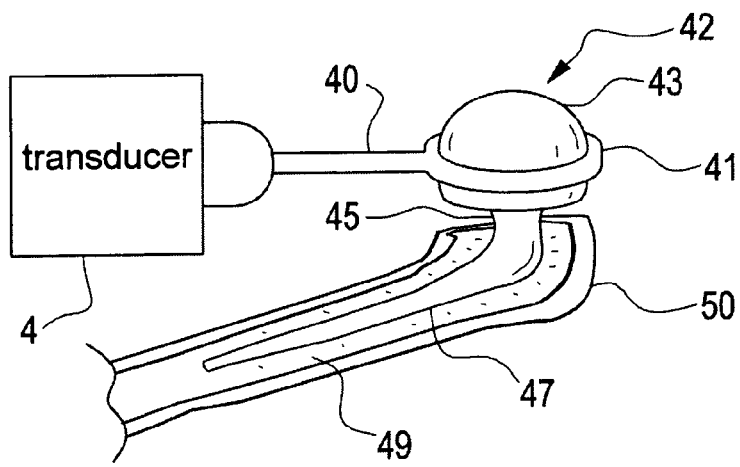

FIGS. 4A and B show a tip 41 of the horn 40 shaped like a ring 41 that fits around the head 43 of a shoulder implant 42. Also shown are the neck 45 of the artificial shoulder implant 42 and the stem 47 of the artificial shoulder implant. The artificial shoulder joint is held in place by bone cement 49 within the bone 50. The ring shaped horn tip 41 can be a partial ring or a ring that can open and close through a hinge mechanism or by being amenable to flexible manipulation.

Figure 4C:
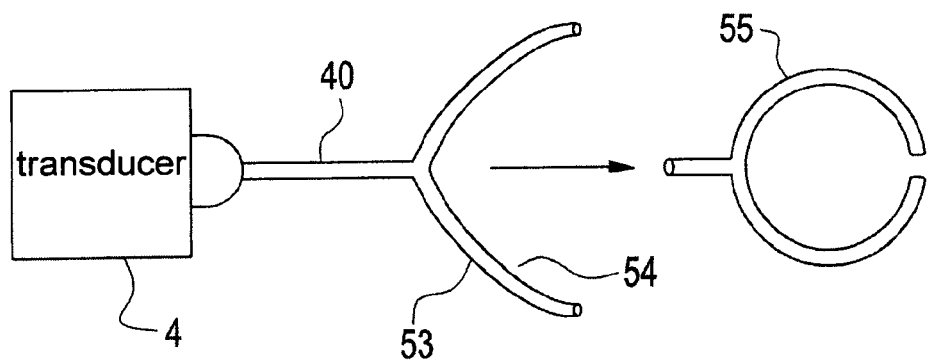

FIG. 4C shows a partial ring shaped horn tip 53 in an open position 54 and shows that ring shaped horn tip in a closed position 55. The power supply 1 provides power to the transducer 4 that produces ultrasonic vibrations through the horn 40 and tip 53 that is closed 55 around the head 43 of the artificial joint 42. That in turn transmits the vibrations down through the neck 45 of the artificial joint 42. That in turns transmits the vibration down through the stem 47 of the artificial joint, causing the implant 42 to be released from the hold of the bone cement 49, so that the implant 42 can be removed from the bone 50.

Figure 5A:
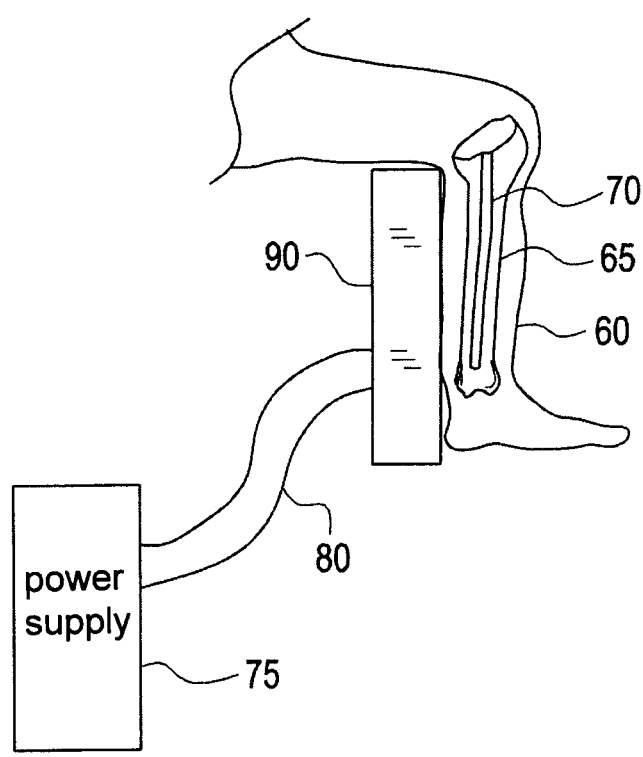
FIGS. 5A and B shows apparatus for application of vibrations to a limb containing an implant.
Figure 5B:
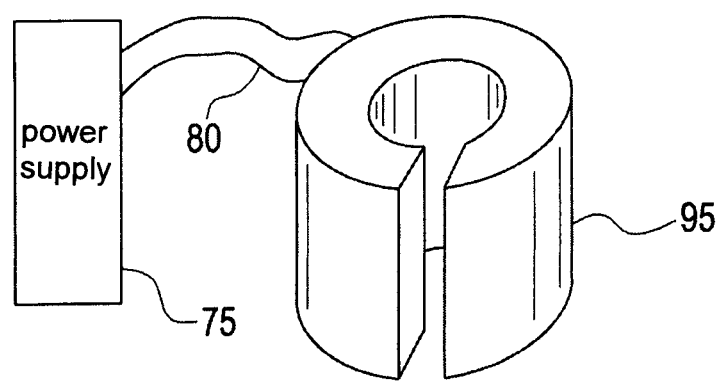

FIG. 5 shows a power supply 75 connected by a wire or wires 80 to a transducer 90 that is placed against a limb such as a leg 60 that has an intramedullary rod 70, normally made of metal, within its bone 65. The transducer also can be made of flexible material or rigid segments connected by flexible joints. The segments encircle a limb for improved efficiency. A flexible transducer 95 as shown in FIG. 5B comes in a variety of sizes and shapes to achieve safe and maximum benefit. The power supply 75 provides power to the transducer 90 or 95 that causes ultrasonic or subsonic vibration to be transmitted through an intact limb 60, causing a heat effect at the interface of the implant 70 and the surrounding bone tissue 65. This results in damage to the tissue at the interface activating tissue destroying cells such as osteoclasts for bone tissue. This damage also may be due to micro-fractures produced by the vibratory or ultrasonic stimulation of 90 or 95. After several weeks the implant will require less force to be removed.

The present invention can be applied to a number of artificial joints, cemented of un-cemented, including those for hip, knee, ankle, shoulder, wrist, elbow and finger joints. The invention is also applicable for removal of screws and implants used for fracture fixation and for stabilizing bone and soft tissues that had been applied as a part of an orthopedic, neurosurgical, vascular and other surgical procedures and to correct deformities. This invention is also applicable for removal of dental, vascular stents, and other soft tissue implants.

The present invention comprises a generator that has a power supply connected to a transducer that produces vibrations from low frequencies of a few hundred Hz. to high frequencies of many thousand Hz. The vibrations are transmitted to horns having sizes and shapes depending on particular applications. Tips of the horns fit the areas of the implants where the horn tips will be attached. For example, a horn tip may have a cup shape to fit the ball joint of a total hip implant. A tip of a horn can also have in the shape of a full or partial ring to transmit the vibrations to the neck area of a femoral component of an artificial hip joint. The ring-shaped tip can be flexible, hinged, or rigid and of a variety of sizes. Similarly, the tip can be concave, convex or combination of both to apply the vibration to the cup of a hip joint to an artificial knee joint or to a shoulder joint. The tip of the horn can also be made of material that molds to the area of application.

The ultrasonic or low frequency vibrator facilitates the removal of a cemented total joint replacement by creating fractures at the bone/bone cement interface and at the implant/bone cement interface. The ultrasonic or low frequency vibrator facilitates the removal of an uncemented total joint replacement by creating fractures at the bone/cement/implant interfaces. The ultrasonic or low frequency device facilitates the removal of intramedullary rods when fractures have healed. The ultrasonic or low frequency device facilitates the removal of bone screws, plates, and other internal fracture fixation devices, once such removal is indicated after healing of a fracture has progressed. The ultrasonic or low frequency device also facilitates implantation of intramedullary rods, bones screws, plates, and other internal fraction fixation devices. The new ultrasonic or low frequency device facilitates the insertion of bone plugs for the fixation of artificial or graft ligament and tendon replacement and facilitates the insertion of other orthopedic and dental implants. The new ultrasonic or low frequency device facilitates the insertion of cardiovascular and other soft tissues and stents.

The new ultrasonic or low frequency device facilitates the removal of other orthopedic and dental implants. The ultrasonic or low frequency of the invention facilitates the removal of stents and implants from cardiovascular and other soft tissues.

A limb or the body part containing the implant is subjected to ultrasonic vibrations above 20,000 Hz or vibratory energy below 20,000 Hz, depending on the particular application. The vibrations produce heating effects at the interface of the implant and the surrounding tissue. This heating is caused as part of the ultrasonic pulse being reflected and dissipated at the interface, due to the mismatch of impedance. This increased temperature will produce thermal damage to the tissue at the interface, activating tissue destroying cells such as osteoclasts for bone tissue. After several weeks, the destroyed tissue will resorb, and the implant will require less force to be removed. This tissue destruction can also be caused by the mechanical damage, due to micro-fractures produced by the vibratory or ultrasonic stimulation.

The ultrasonic device will facilitate removal of intramedullary rods and other implants that are firmly fixed to the bone or other surrounding tissues, making it difficult to be removed by producing controlled damage to the tissue at the interfaces of the rods and implants.

While the invention has been described with reference to specific embodiments, modifications and variations of the invention may be constructed without departing from the scope of the invention, which is defined in the following claims.

I claim:

1. The method comprising facilitating movement of an implant from bone tissue, further comprising generating vibrations and conducting the vibrations from a horn connected to the transducer to the implant by contacting a tip of the horn with the implant, heating an interface of the implant and surrounding tissue or cement, producing thermal damage to the tissue or cement at the interface, making the implant movable by the thermal damage, and moving the implant with respect to the tissue.

2. The method of claim 1, wherein the contacting further comprises contacting a cup-shaped tip of the horn with a head of the implant.

3. The method of claim 2, wherein the contacting further comprises contacting the cup-shaped tip of the horn with a head of an artificial hip implant.

4. The method of claim 1, wherein the contacting further comprises contacting a curved tip of the horn with a curved surface of the implant.

5. The method of claim 1, wherein the contacting further comprises contacting a compliable tip of the horn with the implant.

6. The method of claim 1, wherein the contacting further comprises contacting a ring-shaped tip of the horn around a part of the implant.

7. The method of claim 1, wherein the contacting further comprises contacting a forked compliable tip of the horn with the implant and reforming the compliable tip into a ring shape around a part of the implant before the conducting of the vibrations from the tip of the horn to the implant.

8. The method of claim 1, wherein the moving comprises moving the implant into the tissue.

9. The method of claim 1, wherein the moving comprises removing the implant from the tissue.

10. The method of claim 9, wherein the removal further comprises subsequently removing the implant from the tissue.

11. The method of claim 9, wherein the removal comprises removal of a hip, shoulder, knee, rod, screw, plate, tooth or stent implant in the tissue.

12. The method of claim 1, further comprising placing the transducer horn adjacent a limb of a patient and conducting the vibration through skin, flesh and bone tissue into the implant.

13. The method of claim 12, further comprising pressing a flexible transducer to the limb.

14. The method of claim 12, wherein the transducer horn comprises a conformable horn, further comprising wrapping the conformable horn around the limb.

15. The method of claim 1, wherein producing thermal damage activates tissue destroying osteoclasts.

16. The method of claim 1, wherein the vibrations are ultrasonic vibrations or vibratory energy below 20,000 Hz.

17. Apparatus for facilitating movement of an implant from bone tissue or bone cement, comprising a power supply, a transducer connected to the power supply for generating vibrations, a horn connected to the transducer for conducting the vibrations for heating an interface between the implant and the bone tissue or cement, the horn configured to contact a tip of the horn to a part of the implant before removing the implant from the bone tissue or bone cement.

18. The apparatus of claim 17, wherein the tip further comprises a cup-shaped tip of the horn for fitting a head of the implant.

19. The apparatus of claim 17, wherein the tip further comprises a cup-shaped tip of the horn fitting a head of an artificial hip implant.

20. The apparatus of claim 17, wherein the tip further comprises a curved tip of the horn for contacting a curved surface of the implant.

21. The apparatus of claim 17, wherein the tip further comprises a compliable tip of the horn.

22. The apparatus of claim 17, wherein the tip further comprises a ring-shaped tip of the horn for fitting around a part of the implant.

23. The apparatus of claim 17, wherein the tip further comprises a forked compliable tip of the horn for reforming the compliable tip into a ring shape around a part of the implant before the conducting vibrations from the tip of the horn to the implant.

24. The apparatus of claim 17, wherein the transducer is an ultrasonic transducer which generates ultrasonic vibrations at a frequency of 20 KHz or more.

25. The apparatus of claim 17, wherein the transducer or horn is configured for contacting a body part and for providing the vibrations through skin, flesh and bone of the body part to the implant.

26. The apparatus of claim 25, wherein the transducer or horn has adjustable segments for adjusting to contact the body part.

27. The apparatus of claim 25, wherein the transducer or horn is conformable for wrapping around the body part.

* * * * *